United States Patent [19]

Funk et al.

[11] Patent Number: 5,530,173

[45] Date of Patent: Jun. 25, 1996

[54] PROCESS FOR ALKANE ISOMERIZATION USING REACTIVE CHROMATOGRAPHY AND REACTIVE DESORBENT

[76] Inventors: Gregory A. Funk; Hemant W. Dandekar, both of UOP Research Center 50 E. Algonquin Rd. P.O. Box 5016, Des Plaines, Ill. 60017-5016

[21] Appl. No.: 333,683

[22] Filed: Nov. 3, 1994

[51] Int. Cl.$^6$ .................................................. C07C 5/22
[52] U.S. Cl. .................... 585/737; 585/702; 585/734; 585/736; 585/738; 585/739; 585/741; 585/744; 585/746; 585/748; 585/750; 585/825
[58] Field of Search .................... 585/737, 734, 585/702, 736, 738, 739, 741, 744, 746, 748, 750, 825

[56] References Cited

U.S. PATENT DOCUMENTS

| | | | |
|---|---|---|---|
| 3,122,494 | 2/1964 | Brown et al. | 585/737 |
| 4,783,574 | 11/1988 | Barnes | 585/738 |
| 5,026,950 | 6/1991 | Schmidt et al. | 585/737 |
| 5,055,634 | 10/1991 | Volles | 585/825 |
| 5,146,037 | 9/1992 | Zarchy et al. | 585/738 |
| 5,233,120 | 8/1993 | Minkkinen et al. | 585/737 |
| 5,245,102 | 9/1993 | Zarchy et al. | 585/738 |

OTHER PUBLICATIONS

Badger, C. M. A.; Harris, J. A.; Scott, K. F.; Walker, M. J. Phillips, C. S. G.; *Chromatogr.*, 1976, 126, 11–18. (No Month).

*Primary Examiner*—Asok Pal
*Assistant Examiner*—Walter D. Griffin
*Attorney, Agent, or Firm*—Thomas K. McBride; Eugene I. Snyder; Maryann Maas

[57] ABSTRACT

A process for isomerizing a mixture of alkanes containing pentanes and at least one alkane having from 6 to about 8 carbon atoms and no more than one methyl branch has been developed. The process includes: 1) separating the mixture in a first separation zone to produce two streams, a stream enriched in alkanes having from 6 to about 8 carbon atoms and a stream enriched in pentanes; 2) separating the stream enriched in pentanes in a second separation zone to produce two streams, a stream predominately comprising n-pentane and a stream predominately comprising branched pentanes; 3) passing the stream enriched in alkanes having from 6 to about 8 carbon atoms and the stream enriched in n-pentane to an isomerization zone of a simulated moving bed to produce two streams, a stream containing branched pentanes, n-pentane, and multi-methyl-branched alkanes having from 6 to about 8 carbon atoms, and a stream containing branched pentanes and n-pentane; 4) separating the stream containing branched pentanes, n-pentane, and multi-methyl-branched alkanes having from 6 to about 8 carbon atoms in a third separation zone to produce two streams, a stream enriched in multi-methyl-branched alkanes having from 6 to about 8 carbon atoms and a stream enriched in branched pentanes and n-pentane; and 5) collecting the stream predominately comprising branched pentanes from the second separation zone and the stream enriched in multi-methyl-branched alkanes having from 6 to about 8 carbon atoms from the third separation zone.

12 Claims, 2 Drawing Sheets

PROCESS FOR ALKANE ISOMERIZATION USING REACTIVE CHROMATOGRAPHY AND REACTIVE DESORBENT

BACKGROUND OF THE INVENTION

Alkane isomerization processes are widely used by refiners to convert normal pentane, normal hexane, and monomethyl-branched hexanes into more valuable branched alkanes including mono- and multi-methyl-branched pentanes and multi-methyl-branched hexanes. These more valuable alkanes have a higher octane number and may be used as gasoline blending components to boost the octane number of the gasoline or as intermediates for such oxygenate products as methyl tertiary butyl ether, ethyl tertiary butyl ether, and tertiary amyl methyl ether.

Typically, these processes are one-pass fixed bed operations with the conversion available limited by thermodynamic equilibrium. Two-stage designs, although less common, are also available where the first stage is a fixed bed isomerization reactor and the second stage is a separation unit. See, for example, U.S. Pat. No. 5,146,037 and 5,245,102. The isomerization that takes place in the fixed bed isomerization reactor is limited by thermodynamic equilibrium which results in the reactor effluent containing a substantial amount of unconverted alkanes. The separation unit, which is usually either an adsorption or a fractionation unit, is used to separate the unconverted alkanes from the isomerized products. Generally, the unconverted alkanes are then recycled to the fixed bed isomerization reactor. With this type of design, the recycle stream is usually substantial, and methods of increasing the yield of highly branched alkanes are in demand.

Normal and mono-methyl-branched alkanes containing 7 or more carbon atoms have been converted into benzene and other valuable aromatic hydrocarbons for gasoline blending by catalytic reforming. However, due to environmental concerns, the demand for aromatics in the future may diminish. Although the multi-methyl-branched $C_7$ and $C_8$ isomers are high octane products, the selectivity of normal and mono-methyl-branched $C_7$ and $C_8$ alkanes to their high octane isomers is usually poor due to the extensive cracking. However, applicants' isomerization process is characterized by the removal of the high octane multi-methyl-branched alkanes as formed and a concomitant reduction in cracking, as well as a nearly complete conversion of the reactant alkane feedstock to their multi-methyl-branched isomers, thereby affording an alternate refining process alkane isomerization.

The present invention makes use of both simulated moving bed technology and reactive chromatography to perform the isomerization of alkanes having from 5 to about 8 carbon atoms. Reactive chromatography allows for concurrent isomerization and separation of the unconsumed reactants from the isomerized products thereby extending product yields beyond thermodynamic equilibrium limitations. Others have attempted concurrent alkane isomerization and separation, but only using fixed bed systems. For example, Badger, C. M. A.; Harris, J. A.; Scott, K. F.; Walker, M. J.; Phillips, C. S. G. J. Chromatogr. 1976, 126, 11–18, disclosed placing a catalyst in a gas chromatography column and having a heater move along the length of the column to catalyze isomerization and effect separation.

Also, U.S. Pat. No. 4,783,574 disclosed a fixed bed isomerization reactor containing two sub-beds of adsorbent at opposite ends of the reactor and one sub-bed of catalyst in the center of the reactor. The feed was introduced near the catalyst sub-bed, and a desorbent was introduced at one end of the reactor. The isomerization was catalyzed, and unconsumed reactants were adsorbed on the adsorbent sub-bed downstream of the catalyst sub-bed in the direction of the desorbent flow. Then the desorbent flow was reversed by introducing the desorbent from the opposite end of the reactor to desorb the unconsumed reactants and carry them back to the catalyst sub-bed.

The present invention is significantly distinct from the art. The isomerization zone of the present invention is operated in a simulated moving bed mode incorporating a homogeneous mixture of catalyst and adsorbent in every sub-bed. Also, the invention eliminates the need for a separate desorbent material and desorbent system since the n-pentane desorbent of the present invention is derived from the feed to the process. In addition to being the desorbent, at least a portion of the n-pentane is isomerized to branched pentanes and recovered. The invention further eliminates the recycle of non-isomerized reactants common in the art since, in the present invention, the reactants are retained in the bed until they are isomerized. Finally, the present invention addresses a commercial need for a process which uses normal and mono-methyl-branched alkanes containing from 5 to 8 carbon atoms to produce aliphatic octane boosting compounds for use in gasoline blending.

SUMMARY OF THE INVENTION

The purpose of the invention is to provide a gas phase process for isomerizing a mixture of alkanes containing pentanes and at least one alkane having from 6 to about 8 carbon atoms and no more than one methyl branch, by: 1) separating the mixture in a first separation zone to produce two streams, a stream enriched in alkanes having from 6 to about 8 carbon atoms and a stream enriched in pentanes; 2) separating the stream enriched in pentanes in a second separation zone to produce two streams, a stream predominately comprising n-pentane and a stream predominately comprising branched pentanes; 3) passing the stream enriched in alkanes having from 6 to about 8 carbon atoms and the stream enriched in n-pentane to an isomerization zone of a simulated moving bed to produce two streams, a stream containing branched pentanes, n-pentane, and multi-methyl-branched alkanes having from 6 to about 8 carbon atoms, and a stream containing branched pentanes and n-pentane; 4) separating the stream containing branched pentanes, n-pentane, and multi-methyl-branched alkanes having from 6 to about 8 carbon atoms in a third separation zone to produce two streams, a stream enriched in multi-methyl-branched alkanes having from 6 to about 8 carbon atoms and a stream enriched in branched pentanes and n-pentane; and 5) collecting the stream predominately comprising branched pentanes from the second separation zone and the stream enriched in multi-methyl-branched alkanes having from 6 to about 8 carbon atoms from the third separation zone.

A specific embodiment of the invention is one where the stream enriched in branched pentanes and n-pentane from the isomerization zone and the stream enriched in branched pentanes and n-pentane from the third separation zone are combined with the stream enriched in pentanes from the first separation zone. Another specific embodiment of the invention is one where the simulated moving bed is a mixture of solids effective to isomerize alkane reactants to isomerized alkane products and to selectively adsorb the alkane reactants relative to the isomerized alkane products.

DETAILED DESCRIPTION OF THE INVENTION

Figure 1:
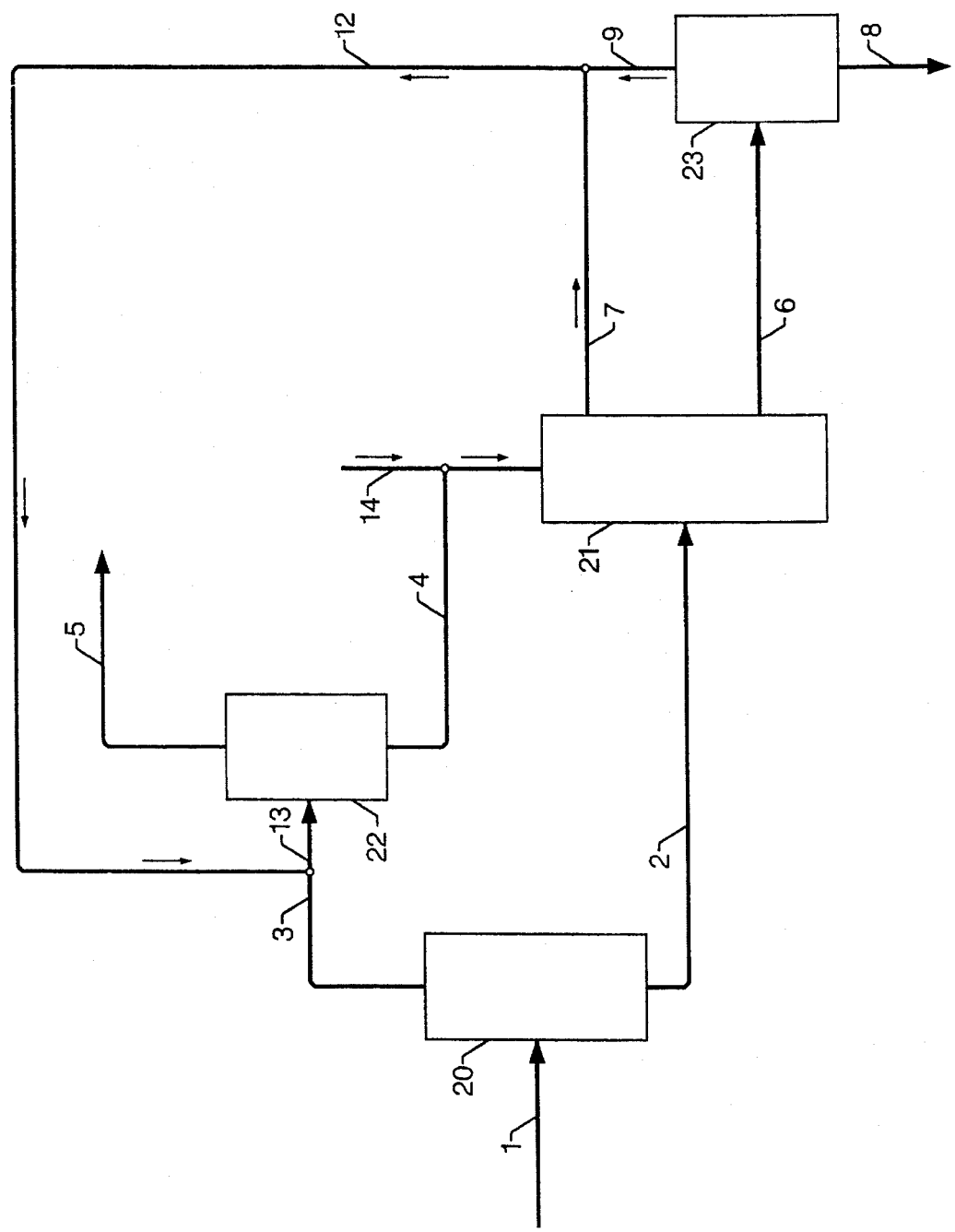
FIG. 1 is a schematic representation of a generic commercial process modified and operated in accordance with the process of this invention.

The invention is a gas phase process for the continuous isomerization of alkanes to form isomerized products where (1) the isomerization zone contains a simulated moving bed to effect reactive chromatography, i.e., an operation where the isomerization reaction is catalyzed concurrently with the unconsumed alkane reactants being separated from the isomerized products, and (2) the desorbent used in the isomerization zone is derived from the process feed, and at least a portion of the desorbent is isomerized.

The feed, which is introduced to the process, contains a mixture rich in normal and/or mono-methyl-branched alkanes containing from 5 to about 8 carbon atoms. At a minimum, the feed contains pentanes and at least one alkane having from 6 to about 8 carbon atoms having no more than one methyl branch. Examples of suitable normal and mono-methyl-branched alkanes include, n-pentane, 2-methylbutane, n-hexane, 2-methylpentane, 3-methylpentane, n-heptane, 2-methylhexane, 3-methylhexane, n-octane, 2-methylheptane, 3-methylheptane, and 4-methylheptane. Preferably the feed contains at least about 50 mole % normal and mono-methyl-branched alkanes. Most preferably, the feed contains greater than about 80 mole percent normal and mono-methyl-branched alkanes. The feed is usually derived from other petroleum processes and is readily available at most refineries. The feed may also be the effluent of a fixed bed alkane isomerization unit where the normal and/or mono-methyl-branched $C_5$ to $C_8$ alkanes and the corresponding isomerized products are present in amounts determined by the conversion in the fixed bed which is limited by thermodynamic equilibrium. For ease of understanding, the alkanes are discussed in terms of pentanes, hexanes, heptanes, and octanes based solely on carbon number regardless of degree of branching unless otherwise specified.

The feed is introduced to a first separation zone where the pentanes are separated from the hexanes, heptanes, and octanes. This separation may be accomplished by any commonly used separation technique. The first separation zone is preferably a fractional distillation unit operating at a pressure in the range of about atmospheric pressure to about 30 psig. The pentanes, having lower boiling points, are removed from one end of the zone, and the hexanes, heptanes, and octanes, having higher boiling points, are removed as a mixture from the opposite end of the zone.

The pentane stream from the first separation zone is introduced to a second separation zone to separate n-pentane from branched pentanes. This separation may be accomplished by any commonly used separation technique. Preferably, the second separation zone is a fractional distillation unit operating at a pressure in the range from about atmospheric pressure to about 30 psig. The branched pentanes, having lower boiling points, are removed from one end of the zone, and the n-pentane, having a higher boiling point, is removed from the opposite end of the zone. The separated branched pentanes are collected since they are valuable octane boosters to be blended with the gasoline pool. The n-pentane is used both as the desorbent and as a reactant in the isomerization zone, as discussed in detail below. Alternatively, the second separation zone may be an adsorption system where the adsorbent solid is selected to either have a pore size capable of admitting n-pentane but not branched pentanes.

The hexane, heptane, and octane stream from the first separation zone and the n-pentane desorbent stream from the second separation zone are separately introduced to an isomerization zone containing a simulated moving bed chromatographic reactor. Typical operating temperatures of the isomerization zone are about 100° C. to about 300° C., preferably from about 200° C. to about 270° C. Typical operating pressures of the isomerization zone are about 6 to about 500 psig, preferably from about 90 to about 325 psig. Both reactive chromatography and simulated moving bed technology are known in the art, and a general discussion of these technologies may be found in Mowry, J. R. In *Handbook of Petroleum Refining Processes;* Meyers, R. A. Ed.; McGraw-Hill: New York, 1986; pp 8–79 to 8–99 for the simulated moving bed technique; and *Preparative and Production Scale Chromatography;* Ganetsos, G., Barker, P. E., Eds.; Chromatographic Science Series Vol. 61; Marcel Dekker: New York, 1993; Chapters 16–21 for reactive chromatography. Applicants are the first to have realized that these technologies may be cooperatively applied effectively in a process to isomerize alkane reactants to form isomerized alkane products.

Reactive chromatography requires that the desired reaction and the separation of the products and reactants occur concurrently. Therefore, the simulated moving bed in the isomerization zone of the present invention must perform dual functions. The mixture of solids forming the simulated moving bed must be effective to catalyze the isomerization reaction and also must be effective as an adsorbent which preferentially retains at least the alkane reactants in order to separate them from the isomerized products. When the hexane, heptane, and octane reactants enter the bed and contact the mixture of solids, they are isomerized and at least dimethyl-branched and trimethyl-branched alkanes are formed. The isomerization reaction primarily takes place in the portion of the solid bed adjacent to and immediately downstream in the direction of the fluid flow of the introduction point of the reactants. Not all the normal and mono-methyl-branched alkanes will immediately react. Since the mixture of solids is also effective as an adsorbent for the reactants, the products and reactants begin to undergo separation. The products which are less strongly adsorbed by the adsorbent are carried with the fluid flow, and the reactants which are strongly adsorbed by the adsorbent are carried countercurrently with the simulated movement of the solids. The migration of the reactants and products in opposite directions results in one region of the bed being rich in reactants and one region of the bed being rich in products. Once separated, the products carried by the fluid flow are removed from the product-rich region in a raffinate stream. Concurrently, the reactants carried by the adsorbent are desorbed at the reactant-rich region by the introduction of a desorbent that is rich in n-pentane. The desorbed reactants, still being in contact with the simulated moving bed, are catalytically isomerized and form additional dimethyl-branched and trimethyl-branched alkanes, which are then carried with the fluid flow and removed. Since the n-pentane desorbent may also be catalytically isomerized, at least a portion of the n-pentane desorbent will form branched pentanes which are removed and collected. The n-pentane isomerization occurs primarily in the portion of the bed adjacent to and immediately downstream in the direction of the fluid flow of the introduction point of the desorbent. The isomerization of the desorbent is desirable not only to obtain the branched alkane product, but also to change the strength of the desorbent within the simulated moving bed. The branched pentanes are less strongly adsorbed than normal pentane. Therefore, the capacity of the adsorbent to adsorb reactants is increased as n-pentane is isomerized to branched pentanes. The isomerization zone operates continuously with the reactants being introduced, the isomerization being catalyzed, the products being separated from reactants and removed, and the reactants being isomerized to form additional products which are also separated and removed. Due to the immediate separation and removal of the products, the thermodynamic equilibrium constraint of a static system is no longer a limiting factor and the isomerization continues, resulting in a much greater conversion to isomerized products. As a result, the external recycle of unconsumed reactants is greatly reduced or eliminated, thereby affording a substantial savings in operating costs.

As previously discussed, the simulated moving bed is made up of a mixture of solids which together are effective both to catalyze the isomerization reaction and to separate the isomerized products from the alkane reactants. Two or more solids, at least one being an isomerization catalyst and at least one being an adsorbent, are used as a homogeneous mixture. A wide variety of solid catalysts and adsorbents are available, and each isomerization application may require a different combination of solids. The solid or solids acting as a catalyst may be any of the commonly used isomerization catalysts including, but not limited to, platinum on mordenite, platinum and aluminum chloride on alumina, and platinum on sulfated metal oxides such as zirconia. See generally, Kirk-Othmer *Encyclopedia of Chemical Technology*, 3rd ed.; Grayson, M., Eckroth, D., Eds.; John Wiley & Sons: New York, Vol. 11 p. 664, Vol. 12 p. 922, and Vol. 15 p. 651. Depending upon the composition of the reactant stream, several different catalysts may be combined in order to accomplish the catalysis function. The preferred catalyst is platinum on mordenite. The adsorbent solid or solids are selected to either have a pore size capable of admitting normal alkanes and mono-methyl-branched alkanes but not more highly branched alkanes, or an affinity for alkanes with no or low branching. Examples of suitable adsorbents include, but are not limited to, silicalite, ferrierite, Ca-A zeolite, MAPO-31, SAPO-31 and SAPO-11 and combinations thereof. Depending upon the composition of the reactant stream, several different adsorbents may be combined in order to accomplish the separation function. The preferred adsorbent is silicalite. Different isomerizations and separations may require different volume ratios of catalyst to adsorbent or different catalyst and adsorbent combinations. Typically, the catalyst to adsorbent volume ratio is in the range of about 1:19 to about 19:1 with a preferred range of from about 1:9 to about 9:1.

The catalyst and adsorbent mixture of solids, once chosen, is used in the isomerization zone in the form of a simulated moving bed where the bed is held stationary, and the locations at which the various streams enter and leave the bed are periodically moved. The bed itself is usually a succession of fixed sub-beds, and different size systems may require differing numbers of sub-beds. The most commonly used range is from about 4 sub-beds to about 24 sub-beds, with the preferred range being from about 6 to about 24 sub-beds, and the most preferred range being from about 6 to about 8 sub-beds. The sub-beds are housed in individual interconnected chambers, and each chamber is equipped with appropriate inlet and outlet lines.

The shift in the locations of input and output streams in the direction of the fluid flow through the bed simulates the movement of the solid bed in the opposite direction. Commercially, moving the locations of the input and output streams may be accomplished by a variety of fluid directing devices such as rotary valves or a network of two-position or multi-position valves which work in conjunction with the inlet and outlet lines of the sub-beds. The fluid directing device accomplishes moving the input and output stream locations through first directing the introduction or withdrawal streams to inlet or outlet lines of the sub-beds. After a specified time period called the step time, the fluid directing device advances one index and redirects the streams to the inlet or outlet line immediately adjacent and downstream of the previously used inlet or outlet line. Each advancement of the fluid directing device to a new position is generally called a step, and the completion of all the valve steps is called a cycle. The step time is uniform for each step in a cycle, and the cycle time ranges generally from about 5 minutes to about 3 hours.

The principal inputs and outputs of the simulated moving bed system consist of four streams: the desorbent, the reactants, the extract, and the raffinate. Each stream flows into or out of the simulated moving bed at individual locations and at a particular flow rate which is independently controlled. The reactant stream, which is introduced to the simulated moving bed system, contains the mixture of hexanes, heptanes, and octanes that were obtained in the first separation zone.

The desorbent, which is introduced to the simulated moving bed system, contains the n-pentane that was obtained in the second separation zone along with some branched pentanes. Using n-pentane as a desorbent brings added benefits which are not readily apparent and which derive from the isomerization of n-pentane incident to its use as a desorbent. In particular, the branched pentanes which result from isomerization are themselves octane boosters which may be blended into gasoline, thereby achieving an incremental octane increase beyond that achieved through isomerization of the alkanes having 6 to about 8 carbon atoms.

Another quite unexpected benefit arises from the differential desorption capability of the branched pentanes relative to n-pentane. Isomerization of n-pentane occurs predominately in the portion of the simulated moving bed adjacent to and downstream in the direction of the fluid flow of the desorbent input. Since the branched pentanes are less strongly adsorbed by the adsorbent than is the n-pentane, there is as a consequence a greater adsorption capacity for reactants resulting in a more efficient separation. Also, because the desorbent is derived from the feed to the process, the present invention eliminates the need for an independent desorbent material and desorbent delivery and recovery system which are common in the art.

The extract and the raffinate are both withdrawn from the simulated moving bed system. The raffinate contains n-pentane desorbent and the isomerized products which were less strongly adsorbed by the bed and were carried with the fluid flow. Examples of the isomerized products found in the raffinate include, 2,3-dimethylbutane, 2,2-dimethylbutane, 2,2-dimethylpentane, 3,3-dimethylpentane, 2,3-dimethylpentane, 2,4-dimethylpentane, 2,2,3-trimethylbutane, 2,2-dimethylhexane, 3,3-dimethylhexane, 2,3-dimethylhexane, 3,4-dimethylhexane, 2,4-dimethylhexane, 2,5-dimethylhexane, 2,2,3-trimethylpentane, 2,3,3-trimethylpentane, 2,3,4-trimethylpentane, and 2,2,4-trimethylpentane. Isomerized products derived from the n-pentane desorbent, 2-methylbutane and 2,2-dimethylpropane, may also be found in the raffinate. It is possible for the isomerization reaction to produce ethyl-branched alkanes which then may be present in the raffinate stream. It is more difficult to form the ethyl-branched alkanes than the methyl-branched alkanes so that if any ethyl-branched alkanes are present in the raffinate they are expected to be at low concentrations. If any ethyl-branched alkanes are formed they are expected to be too large to be adsorbed by the adsorbent and therefore will travel with the fluid flow. Examples of possible ethyl-branched products include 3-ethylpentane and 3-ethylhexane.

The extract contains mainly undesired by-products from cracking, n-pentane desorbent, and branched pentanes. Undesired cracking of the hexanes, heptanes, and octanes may occur in the simulated moving bed, and the products of the cracking may be removed in the extract stream. Some of the separated reactants which were selectively adsorbed by the bed and then desorbed by the desorbent and some of the isomerized products may also be present in the extract stream.

The four principal streams are spaced strategically throughout the simulated moving bed system and divide the sub-beds into three zones. For ease of understanding the different functions occurring in each zone are discussed, however, the process is continuous and there may be a substantial overlap of functions between zones. Zone I contains the sub-beds located between the reactant input and the raffinate output, and the majority of the isomerization of the hexanes, heptanes and octanes, and the selective adsorption of the reactants takes place in this zone. Zone II contains the sub-beds located between the extract output and the reactant input, and some of the isomerization reaction, the desorption of the less selectively adsorbed isomerized products, and the continued adsorption of the selectively adsorbed reactants take place in this zone. Zone III contains the sub-beds located between the desorbent input and the extract output, and the selectively adsorbed reactants are desorbed and catalytically isomerized in this zone. The desorption may serve to restore the adsorption capacity of the adsorbent solids in addition to allowing the selectively adsorbed reactants to be desorbed and isomerized. The isomerization of some of the n-pentane desorbent to form branched pentanes also occurs in Zone III.

As an option, the n-pentane desorbent stream may be split into two streams. The first stream is as described above, and the second n-pentane desorbent stream may be introduced to the simulated moving bed between the reactant input and the raffinate output or between the extract output and the reactant input. This second desorbent stream would function to reduce the residence time of the isomerized products and thereby minimize cracking of the higher carbon number products.

The raffinate stream from the isomerization zone is then directed to a third separation zone where the highly branched hexanes, heptanes, and octanes are separated from the pentanes. This separation may be accomplished by any commonly used separation technique. Preferably, the third separation zone is a fractional distillation unit operating at pressures from about atmospheric to about 30 psig. The pentanes, having lower boiling points, are removed from one end of the zone, and the hexanes, heptanes, and octanes, having higher boiling points, are removed from the opposite end of the zone. The separated highly branched hexanes, heptanes, and octanes are collected since they are valuable octane boosters to be blended with the gasoline pool. The pentanes may be recycled to combine with the first separation zone pentane stream.

The extract stream from the isomerization zone may be recycled to combine with the first separation zone pentane stream which is then conducted to the second separation zone. In the second separation zone, any branched pentanes formed in the isomerization zone will be separated from n-pentane and collected. Any products from cracking will also be separated from the n-pentane and will be collected with the branched pentanes. Alternatively, a portion of the extract stream may be combined with the raffinate stream and passed to the third separation zone. This variant may be employed where the extract stream contains hexanes, heptanes, or octanes, as well as pentanes, and it is desired to separate the hexanes, heptanes, and octanes from the pentanes.

Without intending any limitation on the scope of the present invention and as merely illustrative, this invention is explained below in specific terms as applied to one specific embodiment of the invention as depicted in the figures. Theoretical flow rates and compositions of the streams in FIG. 1 are provided in the table.

Referring now to FIG. 1, the feed, which is conducted in line 1, is introduced to the first separation zone 20. First separation zone 20 is a fractional distillation unit operated at atmospheric pressure. The pentanes of the feed, having lower boiling points, will be separated from the hexanes, heptanes, and octanes which have higher boiling points. The pentanes will be conducted in line 3 while the hexanes, heptanes, and octanes will be conducted in line 2. The hexanes, heptanes, and octanes will be used as reactants in isomerization zone 21.

The pentanes in line 3 will be combined with the stream in line 12 to form a combined stream in line 13 which is introduced to a second separation zone 22. Second separation zone 22 is a fractional distillation unit operated at atmospheric pressure. Branched pentanes will be removed from the second separation zone in line 5 and n-pentane will be removed from the second separation zone in line 4. The branched pentanes in line 5 will be collected for use as octane boosters in blended gasoline. The n-pentane will be used as a desorbent and as a reactant in isomerization zone 21. Hydrogen from line 14 is added to the n-pentane in line 4 to provide catalyst stability in isomerization zone 21.

Figure 2A:
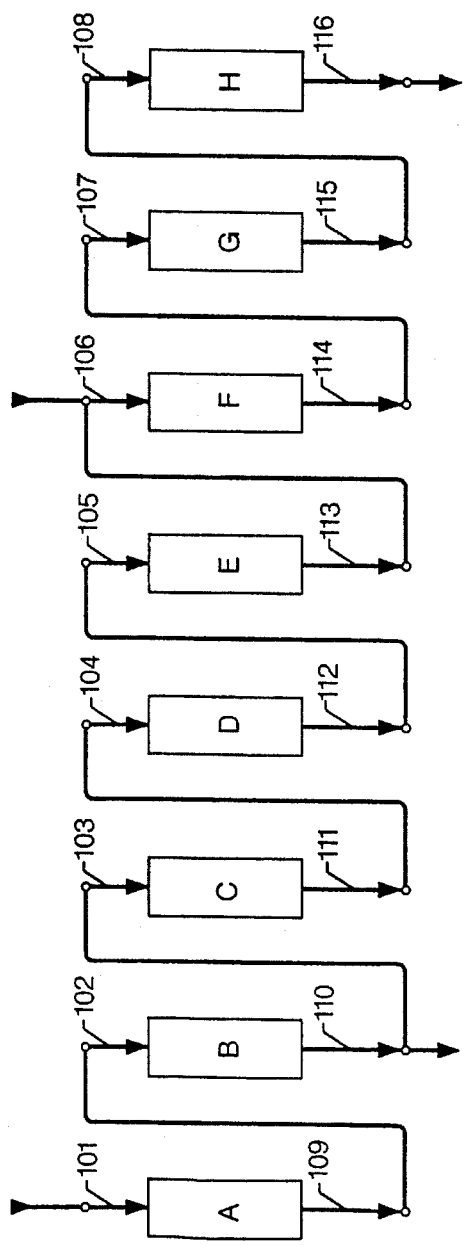
FIG. 2A and 2B depict two schematic representations of a generic isomerization zone at two different points in time modified and operated in accordance with the process of this invention. The figures have been simplified by the deletion of a large number of pieces of apparatus customarily employed on a process of this nature which are not specifically required to illustrate the performance of the subject invention.
Figure 2B:
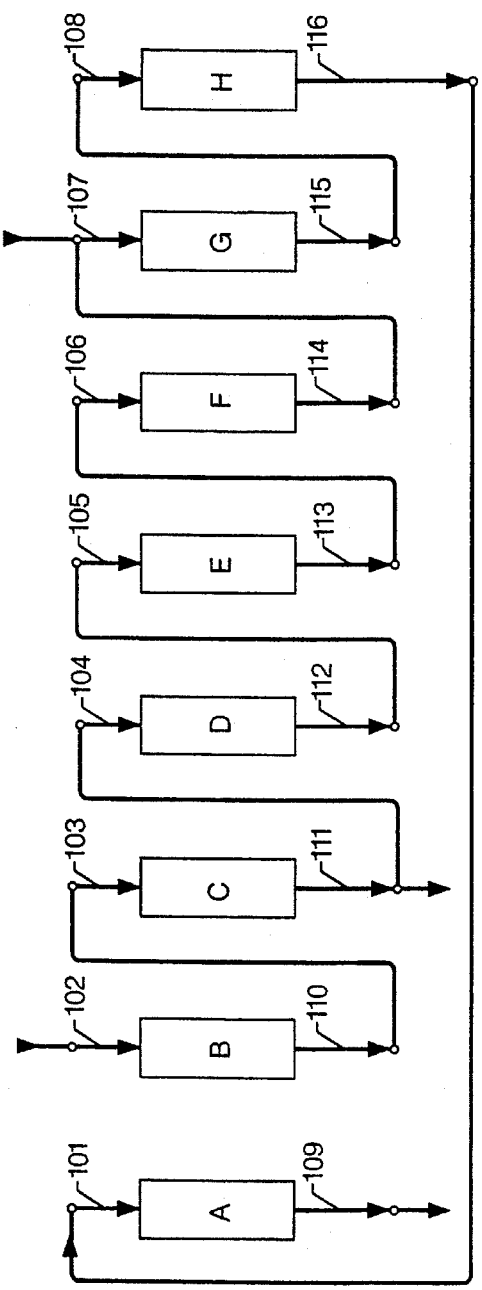

The n-pentane desorbent in line 4 and the hexane, heptane, and octane reactants in line 2 are separately introduced to isomerization zone 21 which contains a simulated moving bed chromatographic reactor. For ease of understanding, isomerization zone 21 is shown as a unit with two streams, lines 2 and 4, being introduced and two streams, lines 6 and 7, being withdrawn. Each stream 2, 4, 6 and 7 is actually connected to a fluid directing and flow control apparatus (not shown) within the isomerization zone. The details of the simulated moving bed chromatographic reactor in the isomerization zone are shown in FIGS. 2A and 2B. Referring now to FIGS. 2A and 2B, the simulated moving bed is made up of eight sub-beds, labeled A–H. Each sub-bed is provided with an inlet line, indicated as 101–108 and an outlet line indicated as 109–116. Each inlet line may be used to introduce the n-pentane desorbent, introduce the hexane, heptane, and octane reactants, or introduce the effluent from the previous sub-bed. Each outlet line may be used to withdraw the extract, withdraw the raffinate, or conduct the effluent to the next sub-bed. Each of the inlet and outlet lines are connected to the fluid directing and flow control apparatus (not shown). The fluid directing apparatus allows the principal streams, the hexane, heptane, and octane reactants, the n-pentane desorbent, the extract and the raffinate, to be sequentially directed to the next successive sub-bed in the direction of the fluid flow. The continued progression of the streams will simulate the movement of the solid bed in the countercurrent direction. The fluid directing apparatus may also control the interconnection of the sub-beds.

FIG. 2A shows the inlet and outlet lines at the starting position. The n-pentane desorbent, after passing through the fluid directing apparatus (not shown), is introduced to the simulated moving bed through inlet line 101, and the hexane, heptane, and octane reactants, after passing through the fluid directing apparatus, are introduced to the simulated moving bed through inlet line 106. The extract is withdrawn from the simulated moving bed through outlet line 110 and passed to the fluid directing apparatus, and the raffinate is withdrawn from the simulated moving bed through outlet line 116 and passed to the fluid directing apparatus. The effluent of sub-beds A through G are conducted through the outlet line of each sub-bed, lines 109–115 respectively, and connected to the inlet line of the next successive sub-bed, lines 102–108 respectively, in order to conduct the effluent from sub-bed to sub-bed. The effluent of the sub-bed from which the raffinate is withdrawn, H, is not routed to the next successive sub-bed since the entire effluent is collected as the raffinate. Breaking the interconnections at this point also prevents backflow of the desorbent being introduced at the inlet of the next successive sub-bed, A.

To demonstrate the progression of the simulated moving bed, FIG. 2B, shows the configuration of the lines after the fluid directing apparatus has advanced one step. Now the n-pentane desorbent is introduced to the simulated moving bed through inlet line 102, and the hexane, heptane, and octane reactants are introduced to the simulated moving bed through inlet line 107. The extract is withdrawn from the simulated moving bed through outlet line 111 and the raffinate is withdrawn from the simulated moving bed through outlet line 109. The effluent of sub-beds B through H are conducted through the outlet line of each sub-bed, lines 110–116 respectively, and connected to the inlet line of the next successive sub-bed, lines 103–108 and line 101 respectively, in order to conduct the effluent from sub-bed to sub-bed. The effluent of the sub-bed from which the raffinate is withdrawn, A, is not routed to the next successive sub-bed since the entire effluent is collected as the raffinate. Each successive step of the fluid directing apparatus would advance the location of the streams in a similar manner.

The reactive chromatography simulated moving bed is operated as follows. The starting position of the location of the streams is not important; for this illustration the starting position of the streams are as depicted in the diagram labeled FIG. 2A. When the reactant stream containing the hexane, heptane, and octane reactants, conducted in inlet line 106, enters the simulated moving bed sub-bed F and contacts the homogeneous mixture of silicalite and platinum on mordenite in a 3:1 volume ratio, the isomerization reaction is catalyzed, and dimethyl-branched and trimethyl-branched alkanes are formed. The dimethyl-branched and trimethyl-branched alkanes, which are weakly absorbed by the silicalite, are carried with the fluid flow and withdrawn from the bed in the raffinate stream conducted from sub-bed H in outlet line 116. The hexane, heptane, and octane reactants, which are strongly absorbed by the silicalite, are carried with the solid bed in its countercurrent simulated movement thereby being separated from the highly branched products. The hexane, heptane, and octane reactants are desorbed from the silicalite by the n-pentane desorbent which is conducted to sub-bed A through inlet line 101. The hexane, heptane, and octane reactants, once desorbed, again contact the platinum on mordenite catalyst and are isomerized to form additional dimethyl-branched and trimethyl-branched alkane products. The newly formed dimethyl-branched and trimethyl-branched products are carried with the fluid flow and removed in the raffinate stream. Some of the n-pentane desorbent is also catalytically isomerized to form branched pentanes. The extract stream, withdrawn from the sub-bed B and conducted through outlet line 110, contains mainly n-pentane and branched pentanes, and some hexane, heptane, and octane reactants and isomerized products.

Referring now to FIG. 1, the extract stream after passing through the fluid directing apparatus of the isomerization zone (not shown) is conducted in line 7, and the raffinate stream after passing through the fluid directing apparatus of the isomerization zone (not shown) is conducted in line 6. The raffinate stream in line 6 is introduced to a third separation zone 23 which is a fractional distillation unit operated at atmospheric pressure to separate the pentanes from the multi-methyl-branched hexanes, heptanes and octanes. The separated multi-methyl-branched hexanes, heptanes, and octanes are conducted from the third separation zone in line 8 and collected to be used as octane boosters for blended gasoline. The separated pentanes are conducted from the third separation zone in line 9 and are combined with the extract stream in line 7 to form line 12. Line 12 is combined with line 3 to form line 13 and carried to second separation zone 22 for separation and collection of the branched pentanes and recycle of n-pentane.

It must be emphasized that the above description is merely illustrative of an embodiment and is not intended as an undue limitation on the generally broad scope of the invention. Moreover, while the description is narrow in scope, one skilled in the art will understand how to extrapolate to the broader scope of the invention. For example, operation of the invention where a portion of the extract stream is combined with the raffinate stream and conducted to the third separation zone can be readily extrapolated from the foregoing description. Similarly, one skilled in the art would understand how the above process is applied using various catalyst and adsorbent mixtures in the reactive chromatography simulated moving bed of the isomerization zone. Furthermore, the optimum number of sub-beds and the optimum cycle time in the isomerization zone, and the optimum flow rates of the process streams for a given application would be readily determined by one skilled in the art.

TABLE

| COMPONENT (lb/hr) | STREAM NO. | | | | | | | | | | | |
|---|---|---|---|---|---|---|---|---|---|---|---|---|
| | 1 | 2 | 3 | 4 | 5 | 6 | 7 | 8 | 9 | 12 | 13 | 14 |
| Hydrogen | — | — | — | — | 500 | 460 | 40 | — | 460 | 500 | 500 | 500 |
| $C_4$ and lower alkanes | — | — | — | — | 200 | 100 | 100 | — | 100 | 200 | 200 | — |
| mono-methyl-branched $C_5$ alkanes | 1000 | — | 1000 | 5750 | 3950 | 7800 | 900 | — | 7800 | 8700 | 9700 | — |
| normal $C_5$ alkane | 3000 | 100 | 2900 | 3450 | — | 500 | 100 | 50 | 450 | 550 | 3450 | — |
| di-methyl-branched $C_6$ alkanes | 500 | 300 | 200 | 300 | — | 2850 | — | 2750 | 100 | 100 | 300 | — |
| mono-methyl-branched $C_6$ alkanes | 1000 | 1000 | — | — | — | 100 | — | 100 | — | — | — | — |
| normal $C_6$ alkane | 1500 | 1500 | — | 50 | — | 100 | 50 | 100 | — | 50 | 50 | — |
| tri-methyl-branched $C_7$ alkanes | — | — | — | — | — | 1000 | — | 1000 | — | — | — | — |
| di-methyl-branched $C_7$ alkanes | 500 | 500 | — | — | — | 1650 | — | 1650 | — | — | — | — |
| mono-methyl-branched $C_7$ alkanes | 1000 | 1000 | — | — | — | 100 | — | 100 | — | — | — | — |
| normal $C_7$ alkane | 1500 | 1500 | — | 40 | — | 100 | 40 | 100 | — | 40 | 40 | — |
| TOTAL | 10000 | 5900 | 4100 | 9590 | 4650 | 14760 | 1230 | 5850 | 8910 | 10140 | 14240 | 500 |

What is claimed is:

1. A gas phase process of isomerizing a mixture of alkane reactants comprising pentanes and at least one alkane having from 6 to about 8 carbon atoms and no more than one methyl branch, said process comprising:
   a. separating the mixture in a first separation zone to produce two streams, a stream enriched in alkanes having from 6 to about 8 carbon atoms and a stream enriched in pentanes;
   b. separating the stream enriched in pentanes in a second separation zone to produce a stream predominately comprising n-pentane and a stream predominately comprising branched pentanes;
   c. passing the stream enriched in alkanes having from 6 to about 8 carbon atoms and the stream enriched in n-pentane to an isomerization zone of a simulated moving bed to produce a stream containing branched pentanes, n-pentane, and multi-methyl-branched alkanes having from 6 to about 8 carbon atoms, and a stream containing branched pentanes and n-pentane;
   d. separating the stream containing branched pentanes, n-pentane, and multi-methyl-branched alkanes having from 6 to about 8 carbon atoms in a third separation zone to produce a stream enriched in multi-methyl-branched alkanes having from 6 to about 8 carbon atoms and a stream enriched in branched pentanes and n-pentane; and
   e. collecting the stream predominately comprising branched pentanes from the second separation zone and the stream enriched in multi-methyl-branched alkanes having from 6 to about 8 carbon atoms from the third separation zone.

2. The process of claim 1 where the stream enriched in branched pentanes and n-pentane from the isomerization zone and the stream enriched in branched pentanes and n-pentane from the third separation zone are combined with the stream enriched in pentanes from the first separation zone.

3. The process of claim 1 where the simulated moving bed is a mixture of solids effective to isomerize said mixture of alkane reactants to isomerized products and to selectively adsorb the alkane reactants relative to the isomerized products.

4. The process of claim 3 where the solid effective to isomerize alkane reactants to isomerized products is selected from the group consisting of platinum on mordenite, platinum and aluminum chloride on alumina, and platinum on sulfated metal oxides.

5. The process of claim 3 where the solid effective to selectively adsorb the alkanes relative to the isomerized products is selected from the group consisting of silicalite, ferrierite, Ca-A zeolite, MAPO-31, SAPO-31 and SAPO-11.

6. The process of claim 3 where the solids are platinum on mordenite and silicalite in a 1:3 volume ratio.

7. The process of claim 1 where the first, second, and third separation zones are fractional distillation units.

8. The process of claim 1 further comprising removing at least a portion of the stream containing branched pentanes and n-pentane from the isomerization zone and combining the portion with the stream containing branched pentanes, n-pentane, and multi-methyl-branched alkanes having from 6 to about 8 carbon atoms.

9. The process of claim 1 further comprising removing at least a portion of the stream predominately comprising n-pentane and separately passing the portion to the isomerization zone.

10. The process of claim 1 where the stream containing branched pentanes, n-pentane, and multi-methyl-branched alkanes having from 6 to about 8 carbon atoms and the stream enriched in multi-methyl-branched alkanes having from 6 to about 8 carbon atoms further comprise ethyl-branched alkanes having from 7 to 8 carbon atoms.

11. The process of claim 1 where the alkane reactant mixture comprises pentanes and alkanes having from 6 to 7 carbon atoms and no more than one methyl branch.

12. The process of claim 1 where the simulated moving bed further comprises a feed stream, a desorbent stream, a raffinate stream, and an extract stream, each with individual flow control.

* * * * *